US00PP26619P2

(12) United States Plant Patent
Garcia-Espana Serra

(10) Patent No.: US PP26,619 P2
(45) Date of Patent: Apr. 19, 2016

(54) ***NERIUM* PLANT NAMED 'JUWEL'**

(50) Latin Name: *Nerium oleander*
Varietal Denomination: Juwel

(71) Applicant: Vital Garcia-Espana Serra, Valencia (ES)

(72) Inventor: Vital Garcia-Espana Serra, Valencia (ES)

(73) Assignee: Tierra Verde CB, Valencia (ES)

( * ) Notice: Subject to any disclaimer, the term of this patent is extended or adjusted under 35 U.S.C. 154(b) by 16 days.

(21) Appl. No.: 14/121,201

(22) Filed: Aug. 11, 2014

(51) Int. Cl.
*A01H 5/02* (2006.01)

(52) U.S. Cl.
USPC ..... Plt./233

(58) Field of Classification Search
USPC ..... Plt./233
CPC ..... A01H 5/02; A01H 5/00
See application file for complete search history.

*Primary Examiner* — Kent L Bell
(74) *Attorney, Agent, or Firm* — C. A. Whealy

(57) ABSTRACT

A new and distinct cultivar of *Nerium* plant named 'Juwel', characterized by its broadly upright plant habit; strong and thick branches that resist bending from the weight of the flowers; dense foliage; freely flowering habit; dark pink-colored flowers; and relative tolerance to low temperatures.

2 Drawing Sheets

Botanical designation: *Nerium oleander.*
Cultivar denomination: 'JUWEL'.

BACKGROUND OF THE INVENTION

The present invention relates to a new and distinct cultivar of *Nerium* plant, botanically known as *Nerium oleander*, grown commercially as a potted plant and hereinafter referred to by the name 'Juwel'.

The new *Nerium* plant is a product of a planned breeding program conducted by the Inventor in Lliria. Valencia, Spain. The objective of the breeding program is to create new *Nerium* plants with strong stems that resist bending from the weight of the numerous attractive flowers.

The new *Nerium* plant originated from an open-pollination, in Lliria. Valencia, Spain in June, 2011 of *Nerium oleander* 'Maurin des Maures', not patented, as the female, or seed, parent with an unknown selection of *Nerium oleander* as the male, or pollen, parent. The new *Nerium* plant was discovered and selected by the Inventor as a single flowering plant from within the progeny of the stated open-pollination in a controlled greenhouse environment in Lliria. Valencia, Spain in May, 2012.

Asexual reproduction of the new *Nerium* plant by terminal cuttings propagated in a controlled greenhouse environment in Lliria. Valencia, Spain since May, 2012 has shown that the unique features of this new *Nerium* plant are stable and reproduced true to type in successive generations of asexual reproduction.

SUMMARY OF THE INVENTION

Plants of the new *Nerium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Juwel'. These characteristics in combination distinguish 'Juwel' as a new and distinct *Nerium* plant:

1. Broadly upright plant habit.
2. Strong and thick branches that resist bending from the weight of the flowers.
3. Dense foliage.
4. Freely flowering habit.
5. Dark pink-colored flowers.
6. Relatively low temperature-tolerant.

Plants of the new *Nerium* differ from plants of the female parent, 'Maurin des Maures', in the following characteristics:

1. Plants of the new *Nerium* are more vigorous than plants of 'Maurin des Maures'.
2. Plants of the new *Nerium* have stronger and thicker branches than plants of 'Maurin des Maures'.
3. Plants of the new *Nerium* have broader leaves than plants of 'Maurin des Maures'.
4. Plants of the new *Nerium* flower ten days later than plants of 'Maurin des Maures'.
5. Plants of the new *Nerium* are more low temperature-tolerant than plants of 'Maurin des Maures'.

Plants of the new *Nerium* can be compared to plants of *Nerium oleander* 'Tito Poggi', not patented. In side-by-side comparisons conducted in Lliria. Valencia, Spain, plants of the new *Nerium* differed from plants of 'Tito Poggi' in the following characteristics:

1. Plants of the new *Nerium* had stronger and thicker branches than plants of 'Tito Poggi'.
2. Plants of the new *Nerium* had broader leaves than plants of 'Tito Poggi'.
3. Plants of the new *Nerium* were more low temperature-tolerant than plants of 'Tito Poggi'.

BRIEF DESCRIPTION OF THE PHOTOGRAPHS

The accompanying photographs illustrate the overall appearance of the new *Nerium* plant showing the colors as true as it is reasonably possible to obtain in colored reproductions of this type. Colors in the photographs may differ slightly from the color values cited in the detailed botanical description which accurately describe the colors of the new *Nerium* plant.

The photograph on the first sheet comprises a side perspective view of a typical flowering plant of 'Juwel' grown in a container.

The photograph on the second sheet is a close-up view of typical flowers of 'Juwel'.

DETAILED BOTANICAL DESCRIPTION

Plants used in the aforementioned photographs and following observations and measurements were grown during the spring with four plants per 17-cm container; plants were initially grown in an outdoor nursery and finished in a polyethylene-covered greenhouse in Lliria. Valencia, Spain and under cultural practices typical of commercial *Nerium* production. During the production of the plants, day temperatures ranged from 5° C. to 35° C. and night temperatures ranged from 2° C. to 25° C. Plants used for the photographs and description were nine months old. In the following description, color references are made to The Royal Horticultural Society Colour Chart, 2007 Edition, except where general terms of ordinary dictionary significance are used.

Botanical classification: *Nerium oleander* 'Juwel'.

Parentage:

*Female, or seed, parent.*—*Nerium oleander* 'Maurin des Maures', not patented.

*Male, or pollen,* parent.—Unknown selection of *Nerium oleander*, not patented.

Propagation:

*Type*.—By terminal cuttings.

*Time to initiate roots, summer*.—About 21 days at temperatures about 25° C.

*Time to initiate roots, winter*.—About 25 days at temperatures about 18° C.

*Time to produce a rooted young plant, summer*.—About 60 days at temperatures about 25° C.

*Time to produce a rooted young plant, winter*.—About 100 days at temperatures about 15° C.

*Root description*.—Medium in thickness, fibrous; white in color.

*Rooting habit*.—Moderate branching; medium density.

Plant description:

*Plant and growth habit*.—Herbaceous perennial grown as a potted plant; broadly upright plant habit; moderately vigorous.

*Branching habit*.—About three main stems develop per plant.

*Plant height*.—About 34.7 cm.

*Plant diameter or spread*.—About 29.8 cm.

*Lateral branches*.—Length: About 24.6 cm. Diameter: Thick, about 6 mm. Internode length: About 2.4 cm. Strength: Strong. Aspect: About 20° from vertical. Texture: Smooth, glabrous. Color: Close to 143B.

Leaf description:

*Arrangement*.—Whorled, simple.

*Length*.—About 8.4 cm.

*Width*.—About 1.8 cm.

*Shape*.—Narrowly lanceolate to elliptic.

*Apex*.—Acute.

*Base*.—Attenuate.

*Margin*.—Entire.

*Texture, upper and lower surfaces*.—Smooth, glabrous.

*Venation pattern*.—Reticulate.

*Color*.—Developing leaves, upper surface: Close to N137C. Developing leaves, lower surface: Close to 146B. Fully expanded leaves, upper surface: Darker than N137A and 147A; venation, close to 145A. Fully expanded leaves, lower surface: Close to 137A and 147B; venation, close to 145A.

*Petioles*.—Length: About 4 mm. Width: About 3 mm. Height: About 2 mm. Texture, upper and lower surfaces: Smooth, glabrous. Color, upper and lower surfaces: Close to 145A.

Flower description:

*Flower form and flowering habit*.—Single flowers arranged in terminal panicles; freely flowering habit with typically about 21 flowers developing per inflorescence; flowers face mostly outwardly to upright.

*Fragrance*.—None detected.

*Natural flowering season*.—Flowering is continuous from the spring through the summer until late summer in Spain; plants begin flowering about five months after planting.

*Flower longevity*.—Flowers maintain good substance for about one week on the plant; flowers not persistent.

*Inflorescence height*.—About 12.2 cm.

*Inflorescence diameter*.—About 12.5 cm.

*Flower diameter*.—About 4.3 cm.

*Flower depth*.—About 4.2 cm.

*Flower buds*.—Length: About 2.8 cm. Diameter: About 6 mm. Shape: Lanceolate to elliptic. Color: Close to 52A and 53A; base, close to 150A to 150B.

*Petals*.—Quantity and arrangement: About five petals arranged in a single whorl; proximal 45% portions of the petals are fused into a tube. Length: About 4.5 cm. Width: About 2 cm. Shape: Roughly spatulate. Apex: Irregularly praemorse. Margin: Entire. Texture, upper and lower surfaces: Smooth, glabrous; velvety. Color: When opening, upper surface: In between N57D and 61D; distally fused portion with stripes, close to 62C to 62D; towards the base, close to 150D. When opening, lower surface: In between N57D and 61D with blotches, close to 53D; distally fused portion, close to 53D; towards the base, close to 150D. Fully opened, upper surface: Close to 61D; distally fused portion with stripes, close to 62C to 62D; towards the base, close to 150D; main color becoming closer to 63C with development. Fully opened, lower surface: Close to 58C with blotches, close to 53D; distally fused portion, close to 53D and 54A; towards the base, close to 150C to 150D.

*Sepals*.—Quantity and arrangement: Five in a single whorl; proximal 25% portions of the sepals are fused into a campanulate-shaped calyx. Length: About 1.5 cm. Width: About 2.5 mm. Shape: Lanceolate. Apex: Narrowly acuminate. Margin: Entire. Texture, upper and lower surfaces: Smooth, glabrous. Color: When opening and fully opened, upper surface: Close to 144B to 144C; towards the margins and base, close to 185B to 185C. When opening and fully opened, lower surface: Close to 144B; towards the margins and base, close to 180A.

*Peduncles*.—Length, primary: About 7.1 cm. Diameter, primary: About 4 mm. Length, secondary: About 4.5 cm. Diameter, secondary: About 3 mm. Strength: Strong. Aspect, primary: Erect. Aspect, secondary:

About 40° from primary peduncle axis. Texture: Smooth, glabrous. Color, upper surface: Close to 144B tinged with close to 180A. Color, lower surface: Close to 144B.

*Pedicels*.—Length: About 6 mm. Diameter: About 1.75 mm. Strength: Strong. Aspect: Erect to about 30° from peduncle axis. Texture: Smooth, glabrous. Color: Close to 144B strongly tinged with close to 180A.

*Reproductive organs*.—Stamens: Quantity: About five per flower. Filament length: About 1.2 cm. Filament color: Close to NN155C. Anther length: About 1.5 cm. Anther shape: Lanceolate. Anther color: Close to 155A. Pollen: Scarce. Pollen color: Close to 155A. Pistils: Quantity: One per flower. Pistil length: About 1.4 cm. Stigma shape: Club-shaped. Stigma color: Close to 146D. Style length: About 1.3 cm. Style color: Close to NN155C; towards the base, close to 63C. Ovary color: Close to 145C to 145D. Fruits and seeds: Fruit and seed development have not been observed on plants of the new *Nerium*.

Disease & pest resistance: Plants of the new *Nerium* have not been observed to be resistant to pathogens and pests common to *Nerium* plants.

Temperature tolerance: Plants of the new *Nerium* have been observed to tolerate high temperatures about 45° C. and to be hardy to USDA Hardiness Zone 6.

It is claimed:

1. A new and distinct *Nerium* plant named 'Juwel' as illustrated and described.

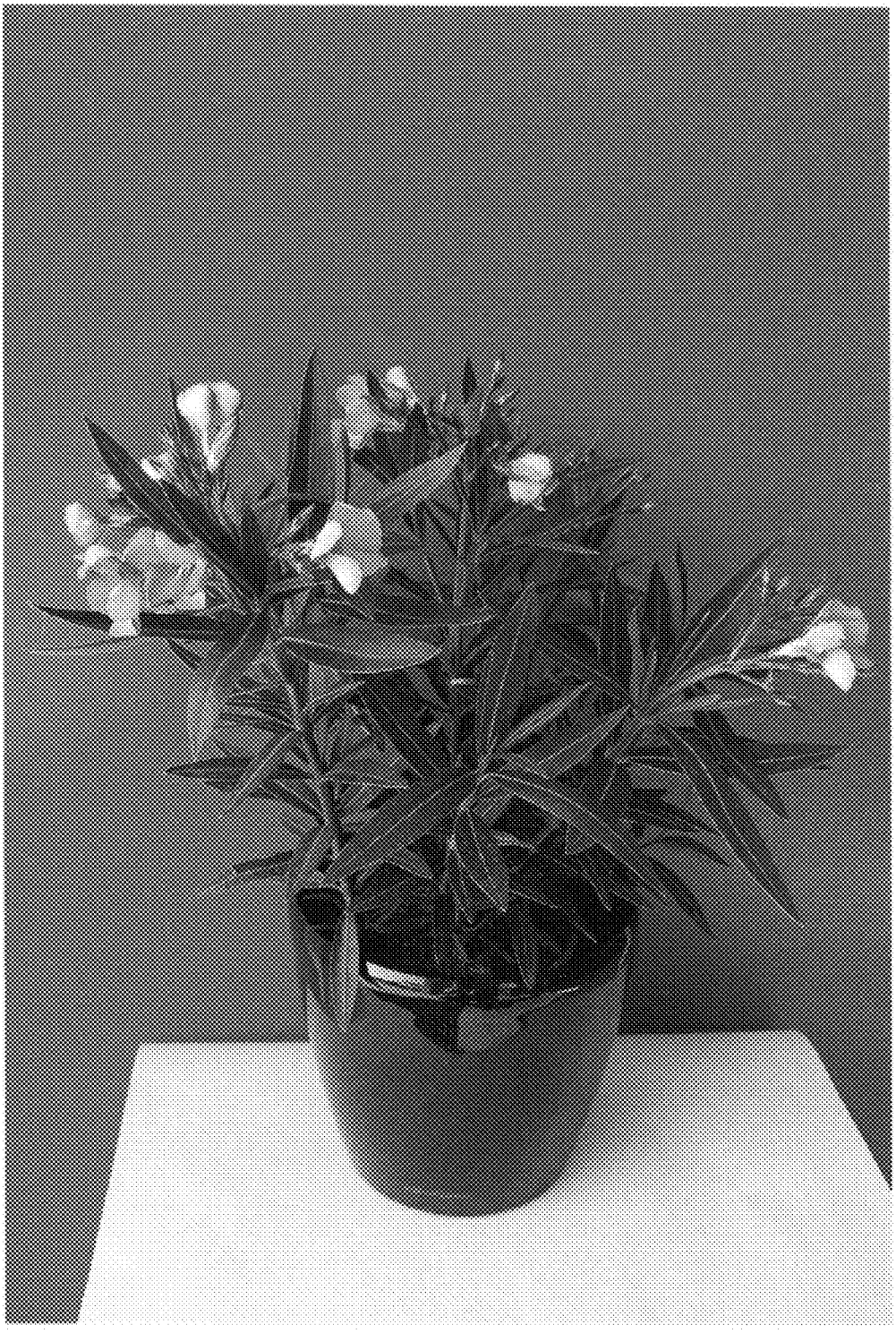

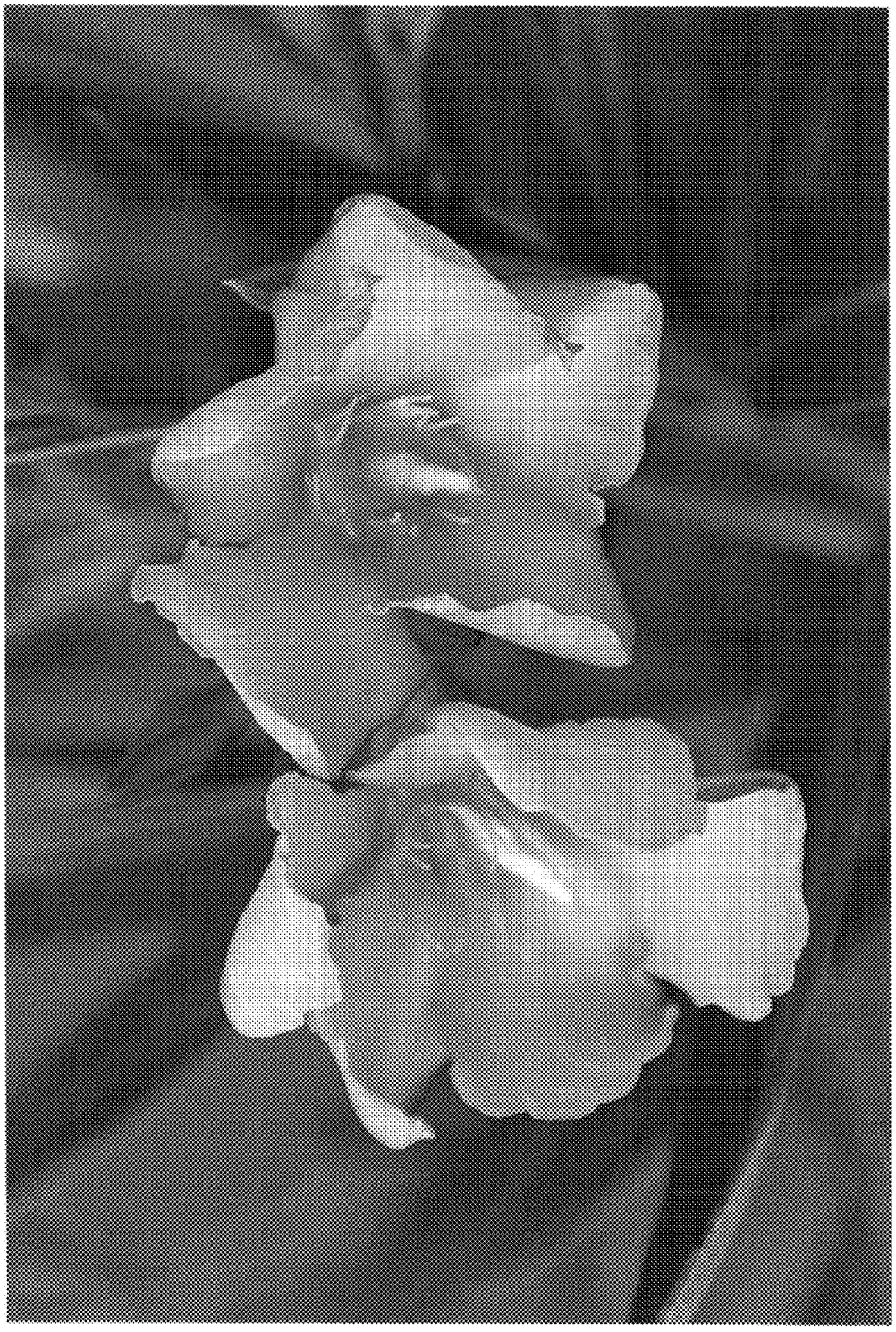

* * * * *